(12) United States Patent
Brundage et al.

(10) Patent No.: US 11,116,878 B2
(45) Date of Patent: Sep. 14, 2021

(54) FLUIDICS ASPIRATION SYSTEM

(71) Applicant: Novartis AG, Basel (CH)

(72) Inventors: Gerry Brundage, Pottsboro, TX (US);
Mark Alan Hopkins, Mission Viejo, CA (US); Pooria Sharif Kashani, Irvine, CA (US); Connor Meehan, Richardson, TX (US)

(73) Assignee: Alcon Inc., Fribourg (CH)

( * ) Notice: Subject to any disclaimer, the term of this patent is extended or adjusted under 35 U.S.C. 154(b) by 152 days.

(21) Appl. No.: 16/173,353

(22) Filed: Oct. 29, 2018

(65) Prior Publication Data

US 2019/0143008 A1 May 16, 2019

Related U.S. Application Data

(60) Provisional application No. 62/587,161, filed on Nov. 16, 2017.

(51) Int. Cl.
*A61M 1/00* (2006.01)
*A61F 9/007* (2006.01)

(52) U.S. Cl.
CPC ....... *A61M 1/0031* (2013.01); *A61F 9/00736* (2013.01); *A61M 1/0035* (2014.02); *A61M 1/0058* (2013.01); *A61M 2205/52* (2013.01); *A61M 2210/0612* (2013.01)

(58) Field of Classification Search
CPC .............. A61M 1/0031; A61M 1/0035; A61M 1/0058; A61M 2210/0612; A61M 2205/52; A61F 9/007; A61F 9/00736
See application file for complete search history.

(56) References Cited

U.S. PATENT DOCUMENTS

| | | | |
|---|---|---|---|
| 5,242,404 A * | 9/1993 | Conley | A61M 1/0031 604/119 |
| 5,267,956 A | 12/1993 | Beuchat | |
| 5,429,601 A | 7/1995 | Conley et al. | |
| 5,697,898 A | 12/1997 | Devine | |
| 6,740,074 B2 | 5/2004 | Morgan | |
| 7,524,299 B2 | 4/2009 | Hopkins | |
| 7,594,901 B2 | 9/2009 | Hopkins | |
| 7,713,237 B2 | 5/2010 | Nazarifar | |
| 8,177,064 B2 | 5/2012 | Mccormick | |
| 8,177,776 B2 | 5/2012 | Humayun | |
| 8,246,580 B2 | 8/2012 | Hopkins | |
| 8,323,271 B2 | 12/2012 | Humayun | |
| 8,430,840 B2 | 4/2013 | Nazarifar et al. | |
| 8,465,467 B2 | 6/2013 | Gao | |
| 8,568,391 B2 | 10/2013 | Kerns | |
| 8,617,106 B2 | 12/2013 | Zacharias | |

(Continued)

FOREIGN PATENT DOCUMENTS

WO WO1993017729 A1 9/1993
WO WO1993018802 A1 9/1993

*Primary Examiner* — Bhisma Mehta
*Assistant Examiner* — James D Ponton

(57) ABSTRACT

A system and method for a diaphragm-based fluidics aspiration system is disclosed. The aspiration system includes a waste reservoir configured to hold a vacuum pressure; an aspiration connection; a vacuum pinch valve including a first outlet fluidically coupled to the waste reservoir; a second outlet fluidically coupled to the aspiration connection; a fluid channel; and an actuator configured to alter a cross-sectional area of the fluid channel.

19 Claims, 4 Drawing Sheets

(56) References Cited

U.S. PATENT DOCUMENTS

| | | |
|---|---|---|
| 8,746,290 B2 | 6/2014 | Hopkins |
| 9,119,699 B2 | 9/2015 | Gordon |
| 9,314,553 B2 | 4/2016 | Gordon |
| 9,561,321 B2 | 2/2017 | Sorensen |
| 9,814,866 B1 * | 11/2017 | Goswami ............ A61M 39/225 |
| 10,195,316 B2 | 2/2019 | Eddo |
| 10,219,940 B2 | 3/2019 | Raney |
| 10,251,983 B2 | 4/2019 | Raney |
| 10,265,443 B2 | 4/2019 | Gerg |
| 10,314,953 B2 | 6/2019 | Ovchinnikov |
| 10,478,532 B2 | 11/2019 | Sussman |
| 10,485,620 B2 | 11/2019 | Kerns |
| 10,537,471 B2 | 1/2020 | Bourne |
| 2005/0118048 A1 * | 6/2005 | Traxinger ........... A61M 1/0058 417/477.2 |
| 2007/0000301 A1 | 1/2007 | Todd |
| 2008/0125695 A1 | 5/2008 | Hopkins |
| 2008/0147023 A1 | 6/2008 | Hopkins |
| 2008/0272023 A1 | 11/2008 | Mccormick |
| 2011/0313343 A1 | 12/2011 | Milutinovic |
| 2012/0157943 A1 | 6/2012 | Sorensen |
| 2014/0238890 A1 | 8/2014 | Kerns |
| 2014/0323813 A1 | 10/2014 | Humayun |
| 2014/0365235 A1 | 12/2014 | Deboer |
| 2014/0378952 A1 | 12/2014 | Humayun |
| 2015/0144514 A1 | 5/2015 | Brennan |
| 2015/0148615 A1 | 5/2015 | Brennan |
| 2017/0326000 A1 | 11/2017 | Heeren |
| 2018/0028359 A1 | 2/2018 | Gordon |
| 2018/0245698 A1 * | 8/2018 | Musolf ..................... F16K 7/07 |

* cited by examiner

1

FLUIDICS ASPIRATION SYSTEM

PRIORITY CLAIM

This application claims the benefit of priority of U.S. Provisional Patent Application Ser. No. 62/587,161 titled "Fluidics Aspiration System", filed on Nov. 16, 2017, whose inventors are Gerry Brundage, Mark Alan Hopkins, Pooria Sharif Kashani and Connor Meehan, which is hereby incorporated by reference in its entirety as though fully and completely set forth herein.

TECHNICAL FIELD

The present invention generally relates to aspiration systems and, in particular, to systems and methods for a fluidics aspiration system.

BACKGROUND

Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is surgery performed on the eye or any part of the eye. Ophthalmic surgery is regularly performed, for example, to repair retinal defects, repair eye muscles, remove cataracts or cancer, or to restore or improve vision. Ophthalmic surgery often requires that fluids and waste, such as vitreous, balanced salt solution (BSS), silicon oil, among others, be aspirated out of the eye.

SUMMARY OF THE INVENTION

In accordance with some embodiments of the present disclosure, an aspiration system is disclosed. The aspiration system includes a waste reservoir configured to hold a vacuum pressure; an aspiration connection; a vacuum pinch valve including a first outlet fluidically coupled to the waste reservoir; a second outlet fluidically coupled to the aspiration connection; a fluid channel; and an actuator configured to alter a cross-sectional area of the fluid channel.

In accordance with another embodiment of the present disclosure, an automated aspiration system is disclosed. The automated aspiration system includes a processor; a vacuum sensor coupled to the processor; and an aspiration system coupled to the vacuum sensor. The aspiration system includes a waste reservoir configured to hold a vacuum pressure; an aspiration connection; a vacuum pinch valve including a first outlet fluidically coupled to the waste reservoir; a second outlet fluidically coupled to the aspiration connection; a fluid channel; and an actuator coupled to the processor and configured to alter a cross-sectional area of the fluid channel; and a positive displacement pump fluidically coupled to the second outlet and the aspiration connection; and a memory communicatively coupled to the processor with computer program instructions stored therein, the instructions configured to, when executed by the processor, cause the processor to actuate the vacuum pinch valve such that a pressure at the aspiration connection is controlled.

In accordance with a further embodiment of the present disclosure, a method for operating an aspiration system is disclosed. The method for operating an aspiration system includes supplying a waste reservoir of an aspiration system with a vacuum pressure; determining a selected pressure at an aspiration connection of the aspiration system; determining a first pressure at the aspiration connection; calculating a first pressure differential based on the selected pressure and the first pressure; and actuating a vacuum pinch valve of the aspiration system, fluidically coupled between the waste reservoir and the aspiration connection, resulting in a second pressure at the aspiration connection such that a second pressure differential based on the selected pressure and the second pressure is smaller in magnitude than the first pressure differential.

BRIEF DESCRIPTION OF THE DRAWING

For a more complete understanding of the present disclosure and its features and advantages, reference is now made to the following description, taken in conjunction with the accompanying drawings, in which.

DETAILED DESCRIPTION

The present disclosure provides an aspiration system that is self-contained and smaller than traditional aspiration systems. The aspiration system may also include an automated aspiration system to allow automatic monitoring and control of pressure in the aspiration system. The aspiration system may be implemented as a stand-alone system or may be included as a module of a surgical console. The aspiration system, as described below, may be used to aspirate fluids and may also be used as a reflux system to remove occlusions or reflux fluids during a surgical procedure.

A further description of the embodiments of the aspiration system, components thereof, and methods of its uses is presented with reference to FIGS. 1 through 4.

Figure 1:
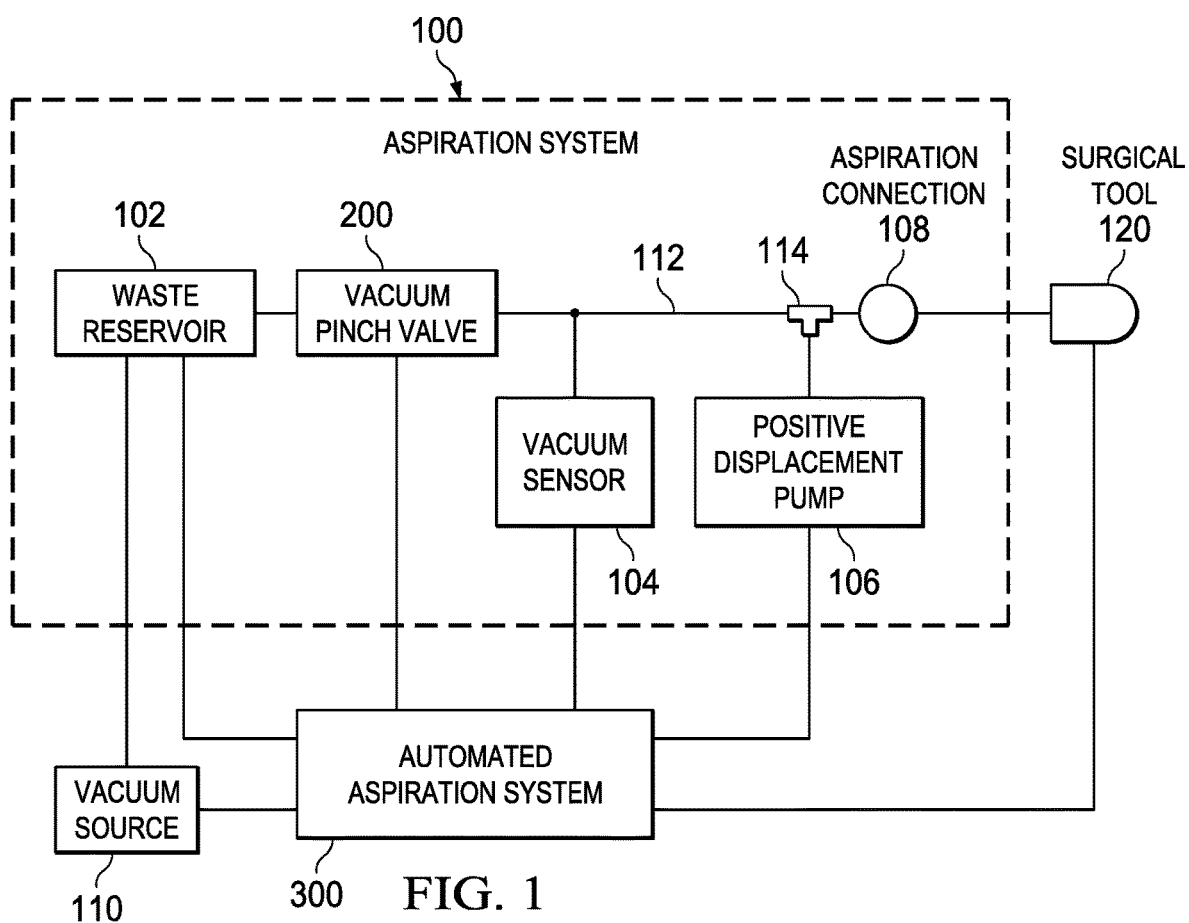
FIG. 1 is a schematic representation of an aspiration system.

FIG. 1 is a schematic representation of an aspiration system. Aspiration system 100 includes waste reservoir 102, vacuum pinch valve 200, vacuum sensor 104, positive displacement pump 106, aspiration connection 108, aspiration line 112, and cut-off valve 114.

Waste reservoir 102 may be used to collect waste fluids during surgical procedures. Waste reservoir 102 may be configured to collect waste fluids, including balanced salt solution (BSS), water, vitreous, silicon oil, air, or other waste materials produced during a surgical procedure. Given that waste reservoir 102 may come into contact with hazardous waste, waste reservoir 102 may be designed for a single use and be disposed of after each procedure or after a small number of procedures. Waste reservoir 102 may be at least partially reusable such that it may be sanitized after use.

As shown in FIG. 1, vacuum pinch valve 200 is fluidically coupled to waste reservoir 102 and aspiration connection 108 by aspiration line 112. Vacuum pinch valve 200 may be actuated to be fully open, fully closed, and open at any percentage between fully open (i.e., 100 percent) and fully closed (i.e., 0 percent) and is configured to control the pressure supplied to aspiration connection 108. While the term "vacuum pinch valve" is used herein, it is to be understood that other valve types (e.g., a rotary valve) may also be used. As described below in reference to FIG. 2, vacuum pinch valve 200 may be actuated such that a pressure less than or equal to the vacuum pressure of waste reservoir 102 is supplied to aspiration connection 108. For example, when vacuum pinch valve 200 is not actuated (e.g., fully open), the vacuum pinch valve does not alter the cross-sectional area or gauge of aspiration line 112 and the full vacuum pressure of waste reservoir 102 is supplied to aspiration connection 108. When vacuum pinch valve 200 is partially actuated, the vacuum pinch valve pinches a flexible portion of aspiration line 112 and effectively reduces the cross-sectional area gauge of the aspiration line. This pinching and resulting reduction in the cross-sectional area or gauge of aspiration line 112 reduces the amount of the vacuum pressure present in waste reservoir 102 that is supplied to aspiration connection 108. When vacuum pinch valve 200 is fully actuated (e.g., fully closed) such that aspiration line 112 is pinched and effectively closed, vacuum pinch valve 200 isolates the vacuum pressure present in waste reservoir 102 from aspiration connection 108 and aspiration connection 108 may not be supplied with any vacuum pressure. Thus, vacuum pinch valve 200 may control the amount of the vacuum pressure of waste reservoir 102 (i.e., the vacuum pressure capacity) that is supplied to aspiration connection 108. Vacuum pinch valve 200 may be configured to proportionally control the pressure supplied to aspiration connection 108. By way of a non-limiting example, vacuum pinch valve 200 may be actuated such that vacuum pinch valve 200 is 10% open, 50% open, or 90% open, resulting in 10%, 50%, or 90%, of the vacuum pressure of waste reservoir 102 is supplied to aspiration connection 108, respectively.

As shown in FIG. 1, vacuum sensor 104 may be coupled between vacuum pinch valve 200 and aspiration connection 108. Vacuum sensor 104 may be coupled to vacuum pinch valve 200 and aspiration connection 108 via a fluidic connection, an electrical connection, a mechanical connection, an optical connection, or any combination thereof. Vacuum sensor 104 may measure the pressure at aspiration connection 108 or at a location along aspiration line 112 between vacuum pinch valve 200 and aspiration connection 108. Vacuum sensor 104 may be one of a variety of invasive or non-invasive pressure sensors known in the art, including but not limited to a piezoelectric pressure sensor, non-contact laser displacement pressure sensor, absolute pressure sensor, a gauge pressure sensor, a vacuum pressure sensor, a differential pressure sensor, or a sealed pressure sensor. In some instances, vacuum sensor 104 may be a single pressure sensor, while, in other instances, vacuum sensor 104 may be multiple pressure sensors. Vacuum sensor 104 may include multiple pressure sensors to provide for a fail-safe if one sensor malfunctions or to improve the accuracy of the pressure measurements of the pressure sensors. A user may select a higher or lower pressure and may cause vacuum pinch valve 200 to be actuated to modify the pressure at aspiration connection 108.

As also shown in FIG. 1, positive displacement pump 106 may be fluidically coupled between vacuum pinch valve 200 and aspiration connection 108. Positive displacement pump 106 may be driven by any suitable actuator, including a stepper motor, an electric motor, a servomotor, a rotary actuator, a linear actuator, or any combination thereof. In some instances, positive displacement pump 106 may include multiple pinch valves configured such that a positive pressure is ultimately supplied by the overall positive displacement pump. Positive displacement pump 106 may be fluidically coupled to a fluid reservoir containing fluid, for example BSS® (balanced salt solution), water, or air and may be configured to provide fluid to the aspiration system between vacuum pinch valve 200 and aspiration connection 108. Positive displacement pump 106 may be used concurrently with vacuum pinch valve 200 to control the pressure that is supplied to aspiration connection 108. When a user requires a change in the pressure at aspiration connection 108, vacuum pinch valve 200 and positive displacement pump 106 may both be actuated to efficiently achieve the required pressure. As described above, positive displacement pump 106 provides fluid to the aspiration system 100. This provided fluid creates a positive pressure within aspiration line 112, which may quickly reduce the pressure at aspiration connection 108. Positive displacement pump 106 may also be actuated to clear waste or fluid that may block the aspiration lines, including aspiration line 112, of aspiration system 100. During a procedure, waste, such as vitreous during a vitrectomy, may become lodged within the fluid lines of the aspiration system 100. Positive displacement pump 106 may be used to create sufficient pressure in the lines to dislodge the waste. For example, positive displacement pump 106 may provide fluid to the aspiration system to increase the pressure within the aspiration lines, including aspiration line 112, to force the waste from the line and into waste reservoir 102. Actuating positive displacement pump 106 allows for a controlled pressure and a controlled volume of fluid to be refluxed to aspiration system 100.

As shown in FIG. 1, cut-off valve 114 may be fluidically coupled to vacuum pinch valve 200, positive displacement pump 106, and aspiration connection 108. Cut-off valve 114 may include, for example, a three-way valve or a four-way valve (other valves are also possible). Cut-off valve 114 may be configured such that both vacuum pinch valve 200 and positive displacement pump 106 remain in fluidic communication with aspiration connection 108. However, cut-off valve 114 may be configured such that vacuum pinch valve 200 is in fluidic communication with positive displacement pump 106 but not aspiration connection 108. Further, cut-off valve 114 may be configured such that vacuum pinch valve 200 is not in fluidic communication with either positive displacement pump 106 or aspiration connection 108. Similarly, cut-off valve 114 may be configured such that positive displacement pump is in fluidic communication with vacuum pinch valve 200 but not aspiration connection 108. Further, cut-off valve 114 may be configured such that positive displacement pump 106 is not in fluidic communication with either vacuum pinch valve 200 or aspiration connection 108.

These various configurations of cut-off valve 114 allow for efficient interaction between each of vacuum pinch valve 200, positive displacement pump 106, and aspiration connection to control the pressure within aspiration system 100 and the pressure supplied to aspiration connection 108. Cut-off valve 114 may be configurable by either a user or by an actuator controlled by automated aspiration system 300, as discussed below in reference to FIG. 3. A user or automated aspiration system 300 may configure cut-off valve 114 throughout a procedure as needed to efficiently control pressures within aspiration system 100. A user may manually configure cut-off valve 114. Automated aspiration system 300 may control an actuator associated with cut-off valve 114 to configure cut-off valve 114. This actuator may be any suitable actuator, including a stepper motor, an electric motor, a servomotor, a rotary actuator, a linear actuator, or any combination thereof.

As shown in FIG. 1, aspiration connection 108 may be fluidically coupled to surgical tool 120. Surgical tool 120 may be a tool requiring aspiration during a surgical procedure. For example, surgical tool 120 may be a vitrectomy probe, an aspirator, an ultrasound, fragmentation, or phacoemulsification handpiece, a suction or soft-tip cannula, an aspirating laser probe or any other surgical tool requiring a vacuum pressure. Aspiration connection 108 may be configured such that surgical tool 120 is supplied with approximately the same pressure that is supplied to aspiration connection 108. Thus, a user may control the pressure of surgical tool 120 by controlling the pressure of aspiration connection 108. Surgical tool 120 may include a pressure control mechanism. For example, surgical tool 120 may include a foot pedal, a pressure-sensitive handle, a push button, or any other mechanism which can effectively communicate a setting change to the aspiration system 100 and components thereof.

Waste reservoir 102 may be connected to vacuum source 110. Vacuum source 110 may be a diaphragm pump, a peristaltic pump, a Venturi pump, or any other pump capable of providing a vacuum. Although vacuum source 110 may be capable of supplying a variable vacuum pressure to waste reservoir 102, in some instances vacuum source 110 may be configured to supply and hold a constant vacuum pressure in waste reservoir 102. A user of aspiration system 100, such as a surgeon or nurse, may require varying pressure levels at aspiration connection 108. The range of required pressures may depend on the type or the stage of the application for which the aspiration system is being used. For example, in an ophthalmic application, the range of pressure may be 0-650 mmHg (millimeters of mercury). As the user changes a setting on a tool to change the selected pressure at the tool, vacuum pinch valve 200 may be actuated to provide different selected pressure levels while the vacuum pressure within waste reservoir 102 remains constant. The vacuum pressure within waste reservoir 102 provides the constant vacuum capacity of aspiration system 100, while vacuum pinch valve 200 proportionally controls the percentage of the vacuum capacity that is supplied to aspiration connection 108. As shown in FIG. 1, vacuum source 110 is external to aspiration system 100. However, in some instances, vacuum source 110 may be integrated within aspiration system 100. Either one or both of vacuum source 110 and waste reservoir 102 may also include pressure sensors to allow for monitoring and/or control of the vacuum pressure.

Figure 3:
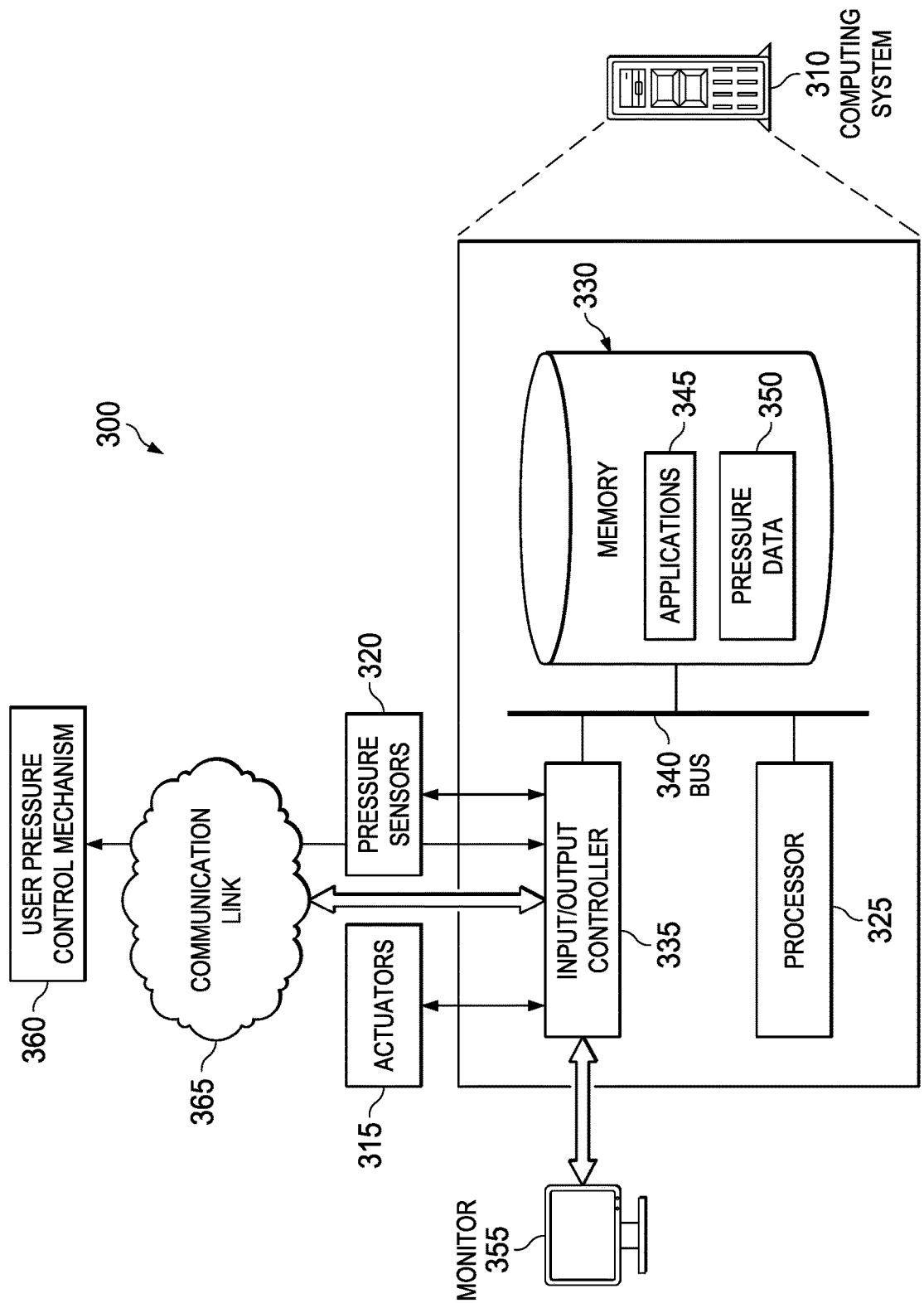
FIG. 3 is a block diagram of an automated aspiration system for the aspiration system shown in FIG. 1.

As shown in FIG. 1, aspiration system 100 may also be communicatively coupled to automated aspiration system 300, as shown in FIG. 3, and described in more detail below. Automated aspiration system 300 may be communicatively coupled to waste reservoir 102, vacuum source 110, vacuum pinch valve 200, vacuum sensor 104, positive displacement pump 106, cut-off valve 114 and/or surgical tool 120. Automated aspiration system 300 may communicate with and control these components in various ways. For example, automated aspiration system 300 may control the actuation of vacuum pinch valve 200 and positive displacement pump 106 based on user inputs at surgical tool 120 by supplying power to vacuum pinch valve 200 and positive displacement pump 106 to actuate vacuum pinch valve 200 and positive displacement pump 106. Automated aspiration system 300 may also communicate with and control cut-off valve 114, and any associated actuator(s), to control the resulting flow within aspiration system 100 from vacuum pinch valve 200, positive displacement pump 106, or both. As a further example, automated aspiration system 300 may receive and store pressure settings and pressure sensor readings from vacuum source 110, waste reservoir 102, and/or vacuum sensor 104. Finally, automated aspiration system 300 may provide a closed-loop control system capable of controlling and maintaining a required pressure at surgical tool 120.

As was described above with reference to waste reservoir 102, other components or parts of a component described above may come into contact with hazardous waste. Therefore, these components may be designed for a single use and may be disposed of after each procedure or after a small number of procedures. For example, aspiration tubing throughout aspiration system 100 may be disposable. However, if aspiration system 100 is hard-molded into a cassette, aspiration channels may be hard-molded channels and, therefore, reusable and non-disposable. For further example, certain parts of vacuum pinch valve 200, vacuum sensor 104, positive displacement pump 106, and aspiration connection 108 may also be disposable. However, aspiration system 100 may also be composed partially or entirely of reusable, non-disposable components.

FIG. 2 is a schematic representation of one example embodiment of vacuum pinch valve 200 in various states of actuation. As shown in FIG. 2, vacuum pinch valve 200 includes a fluid channel 202 and an actuator 204. Fluid channel 202 may be a tube made of a flexible material, for example silicone or polyvinyl chloride (PVC). In other embodiments, fluid channel 202 may include both flexible material and rigid material. In still further embodiments, fluid channel 202 may consist entirely of rigid material. Actuator 204 may be any mechanism capable of increasing and decreasing the cross-sectional area of fluid channel 202. For example, actuator 204 may be a solenoid or other proportional actuator controlled directly by a user input or by automated aspiration system 300 as shown in FIG. 3. Automated aspiration system 300 may actuate actuator 204 to control the pressure supplied to aspiration connection 108 by supplying power to actuator 204 to increase or decrease the cross-sectional area of fluid channel 202. Automated aspiration system 300 may control actuator 204 based on information communicated from various components of aspiration system 100, including, but not limited to, vacuum sensor 104 and surgical tool 120. While fluid channel 202 and actuator 204 are depicted in a single configuration in FIG. 2, other configurations may be possible while achieving the same functionality within the scope of this disclosure. Vacuum pinch valve 200 also includes a first outlet 206, which may be fluidically coupled to waste reservoir 102, and a second outlet 208, which may be fluidically coupled to aspiration connection 108.

Figure 2A:
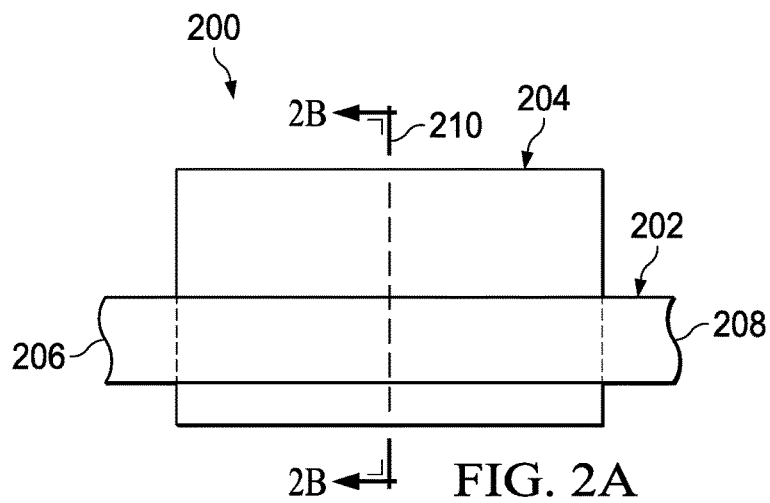
FIGS. 2A, 2C, and 2E are schematic representations of an exemplary embodiment of a vacuum pinch valve of the aspiration system shown in FIG. 1 in various states of actuation.
Figure 2B:
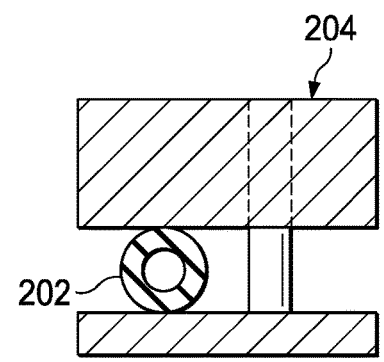
FIGS. 2B, 2D, and 2F are schematic representations of cross-sectional views of the vacuum pinch valve shown in FIGS. 2A, 2C, and 2E.

FIG. 2B shows a cross-sectional view of vacuum pinch valve 200 along centerline 210 shown in FIG. 2A. As shown in FIG. 2A and FIG. 2B, vacuum pinch valve 200 may be configured such that actuator 204 does not alter the cross-sectional area of fluid channel 202. When configured in this way, the full vacuum pressure of waste reservoir 102 may be passed through vacuum pinch valve 200 and supplied to aspiration connection 108. As shown, actuator 204 remains in contact with fluid channel 202 although actuator 204 does not alter the cross-sectional area of fluid channel 202. However, vacuum pinch valve 200 may also be configured such that actuator 204 loses contact with fluid channel 202 in this configuration.

Figure 2C:
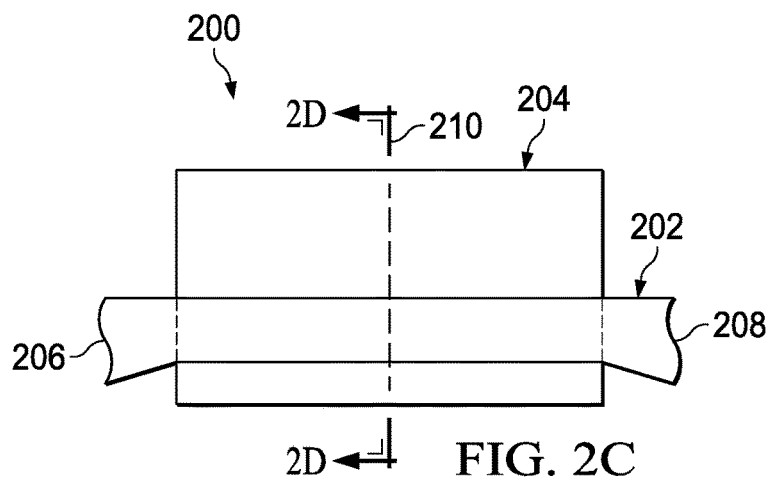
Figure 2D:
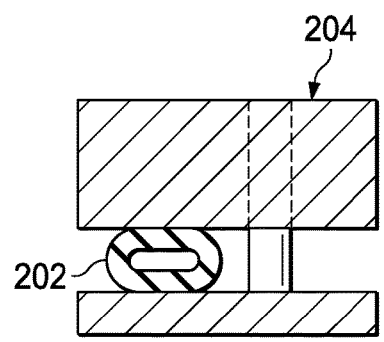

FIG. 2D shows a cross-sectional view of vacuum pinch valve 200 along centerline 210 shown in FIG. 2C. As shown in FIG. 2C and FIG. 2D, vacuum pinch valve 200 may be actuated such that actuator 204 partially reduces or decreases the cross-sectional area of fluid channel 202. Depending on the amount that the cross-sectional area of fluid channel 202 is decreased, a portion of the vacuum pressure of waste reservoir 102 may be passed through vacuum pinch valve 200 and supplied to aspiration connection 108. Although FIG. 2C and FIG. 2D show vacuum pinch valve 200 in a single configuration, vacuum pinch valve may be actuated such that actuator 204 reduces or decreases the cross-sectional area of fluid channel 202 to various degrees. As described above in reference to FIG. 1, vacuum pinch valve may be actuated such that 10%, 50%, 90%, or any other percentage of the vacuum pressure of waste reservoir 102 may be supplied to aspiration connection 108. The actuation of vacuum pinch valve 200 is proportional to the percentage of the vacuum pressure of waste reservoir 102 that is supplied to aspiration connection 108. Thus, when vacuum pinch valve 200 is actuated such that the cross-sectional area of fluid channel 202 is 10%, 50% or 90% of the nominal cross-sectional area, 10%, 50%, or 90% of the vacuum pressure of waste reservoir 102, respectively, may be supplied to aspiration connection 108.

Figure 2E:
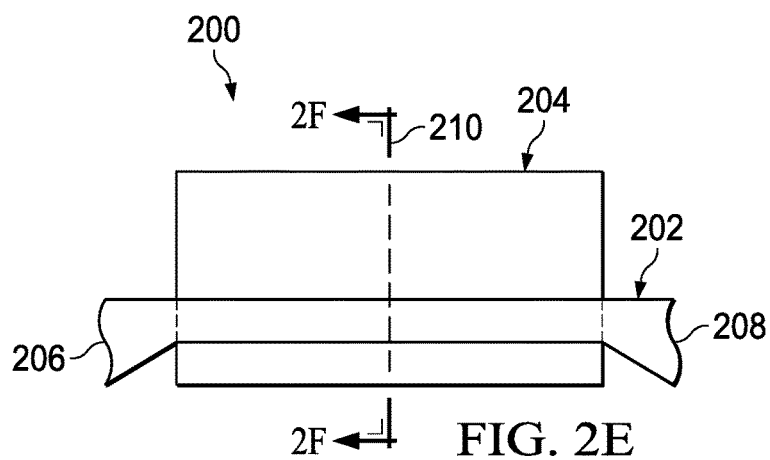
Figure 2F:
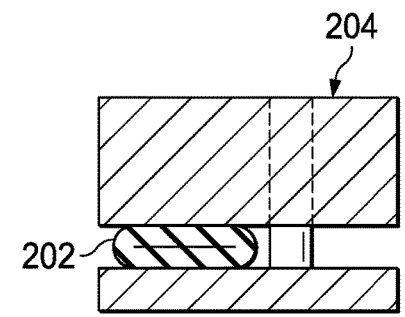

FIG. 2F shows a cross-sectional view of vacuum pinch valve 200 along centerline 210 shown in FIG. 2E. As shown in FIG. 2E and FIG. 2F, vacuum pinch valve 200 may be actuated such that actuator 204 fully reduces the cross-sectional area of fluid channel 202. In this configuration, essentially none of the vacuum pressure of waste reservoir 102 is passed through vacuum pinch valve 200 and supplied to aspiration connection 108. As described above in reference to FIG. 1, certain components of vacuum pinch valve 200 may be disposable. For example, while actuator 204 may be reusable, fluid channel 202 may be designed for a single use and to be disposed of after each procedure or after a small number of procedures. However, both actuator 204 and fluid channel 202 may be reusable, non-disposable components.

As briefly discussed above, FIGS. 2A through 2F show one example embodiment. This embodiment demonstrates the functionality of vacuum pinch valve 200. One of skill in the art would appreciate that other embodiments of vacuum pinch valve 200 are possible within the scope of this disclosure. For example, fluid channel 202 may include both flexible material and rigid material. For further example, actuator 204 may be configured to alter the cross-sectional area of fluid channel 202 in ways other than applying transverse force, as shown in FIGS. 2A through 2F. Actuator 204 may be configured to apply axial or rotational force to fluid channel 202 in order to alter the cross-sectional area. For yet another example, fluid channel 202 and actuator 204 may be included within a rotary valve, which may function in the same way as vacuum pinch valve. In this example embodiment, vacuum pinch valve 200 would control the amount of vacuum pressure supplied through vacuum pinch valve 200 by rotating the rotary valve by way of actuator 204 to increase or decrease the cross-sectional area of fluid channel 202.

FIG. 3 is a block diagram of an automated aspiration system 300 for the aspiration system 100 shown in FIG. 1. Automated aspiration system 300 may include computing subsystem 310, actuators 315, pressure sensors 320, monitor 355, user pressure control mechanism 360, and communication link 365. Actuators 315 may include the actuator 204 of vacuum pinch valve 200 and the motor driving positive displacement pump 106, among others. Pressure sensors 320 may include vacuum sensor 104 and other pressure sensors that may be included within aspiration system 100 or components thereof. Pressure readings of aspiration system 100 may be recorded in pressure data 350, discussed in further detail below.

Pressure sensors 320 may sense the pressure within various parts of aspiration system 100, such as the pressure within aspiration line 112 between vacuum pinch valve 200 and aspiration connection 108.

Pressure sensor 320 may then transmit the pressure to computing subsystem 310 for storage as pressure data 350 as discussed in further detail below. Pressure sensors 320 may be any one of a variety of invasive or non-invasive pressure sensors known in the art. For instance, it may be a piezoelectric pressure sensor, non-contact laser displacement pressure sensor, absolute pressure sensor, a gauge pressure sensor, a vacuum pressure sensor, a differential pressure sensor, or a sealed pressure sensor. The pressure sensor may use mechanical sensors, electrical sensors, or a combination of sensors.

All or part of computing subsystem 310 may operate as a component of, or independent of, aspiration system 100, or independent of any other components shown in FIG. 1. Computing subsystem 310 may include processor 325, memory 330 and input/output controllers 335 communicatively coupled by bus 340. Processor 325 may include hardware for executing instructions, such as those making up a computer program, such as applications 345. As an example and not by way of limitation, to execute instructions, processor 325 may retrieve (or fetch) the instructions from an internal register, an internal cache, and/or memory 330; decode and execute them; and then write one or more results to an internal register, an internal cache, and/or memory 330. This disclosure contemplates processor 325, including any suitable number of any suitable internal registers, where appropriate. Where appropriate, processor 325 may include one or more arithmetic logic units (ALUs); be a multi-core processor; or include one or more processors 325. Although this disclosure describes and illustrates a particular processor, this disclosure contemplates any suitable processor.

Processor 325 may execute instructions, for example, to maintain or control pressure within aspiration system 100. For example, processor 325 may run applications 345 by executing or interpreting software, scripts, programs, functions, executables, or other modules contained in applications 345. Processor 325 may perform one or more operations related to FIG. 4. Input data received by processor 325 or output data generated by processor 325 may include pressure data 350.

Memory 330 may include, for example, random access memory (RAM), a storage device (e.g., a writable read-only memory (ROM) or others), a hard disk, a solid state storage device, or another type of storage medium. Computing subsystem 310 may be preprogrammed or it may be programmed (and reprogrammed) by loading a program from another source (e.g., from a CD-ROM (compact disc read-only memory), from another computer device through a data network, or in another manner). Input/output controller 335 may be coupled to input/output devices (e.g., monitor 355, actuators 315, pressure sensors 320, user pressure control mechanism 360, a mouse, a keyboard, or other input/output devices) and to communication link 365. The input/output devices may receive and transmit data in analog or digital form over communication link 365.

Memory 330 may store instructions (e.g., computer code) associated with an operating system, computer applications, and other resources. Memory 330 may also store application data and data objects that may be interpreted by one or more applications or virtual machines running on computing subsystem 310. For example, pressure data 350 and applications 345 may be stored in memory 330. In some implementations, a memory of a computing device may include additional or different data, applications, models, or other information.

Pressure data 350 may include information related to pressure data captured by pressure sensors 320 that may be used to determine if the pressure within aspiration system 100 is being controlled or maintained correctly. For example, the pressure data may include whether a pressure setting as indicated by a user is being maintained. This pressure data may also include a pressure differential indicating the difference between the actual pressure being sensed by a pressure sensor and the pressure setting as indicated by a user.

Applications 345 may include software applications, scripts, programs, functions, executables, or other modules that may be interpreted or executed by processor 325. Applications 345 may include machine-readable instructions for performing one or more operations related to FIG. 4. Applications 345 may include machine-readable instructions for calculating when the actual pressure within aspiration system 100 is set to the pressure setting as indicated by a user. For example, applications 345 may be configured to analyze the pressure differential between the setting as indicated by a user pressure control mechanism 360 and the actual pressure as indicated by the pressure sensors 320. Applications 345 may generate output data and store output data in memory 330, in another local medium, or in one or more remote devices (e.g., by sending output data via communication link 365).

Communication link 365 may include any type of communication channel, connector, data communication network, or other link. For example, communication link 365 may include a wireless or a wired network, a Local Area Network (LAN), a Wide Area Network (WAN), a private network, a public network (such as the Internet), a wireless network, a network that includes a satellite link, a serial link, a wireless link (e.g., infrared, radio frequency, or others), a parallel link, or another type of data communication network.

Processor 325 may command actuators 315 to move the actuator 204 of vacuum pinch valve 200 to either increase or decrease the cross-sectional area of fluid channel 202. Processor 325 may also command actuators 315 to activate positive displacement pump 106 to provide positive pressure to aspiration system 100. While actuators 315 are controlling actuator 204 and/or positive displacement pump 106, pressure sensors 320 may record pressure data for the various portions of aspiration system 100. Processor 325 may then execute application 345 to control and maintain the pressure(s). Processor 325 may then command actuators 315 to stop actuating actuator 204 and positive displacement pump 106 once the required pressure setting has been achieved. If processor 325 or application 345 determines that automated aspiration system 300 is not properly controlling or maintaining the pressure(s) within aspiration system 100, a warning may be transmitted to monitor 355 and may be displayed to a user.

Figure 4:
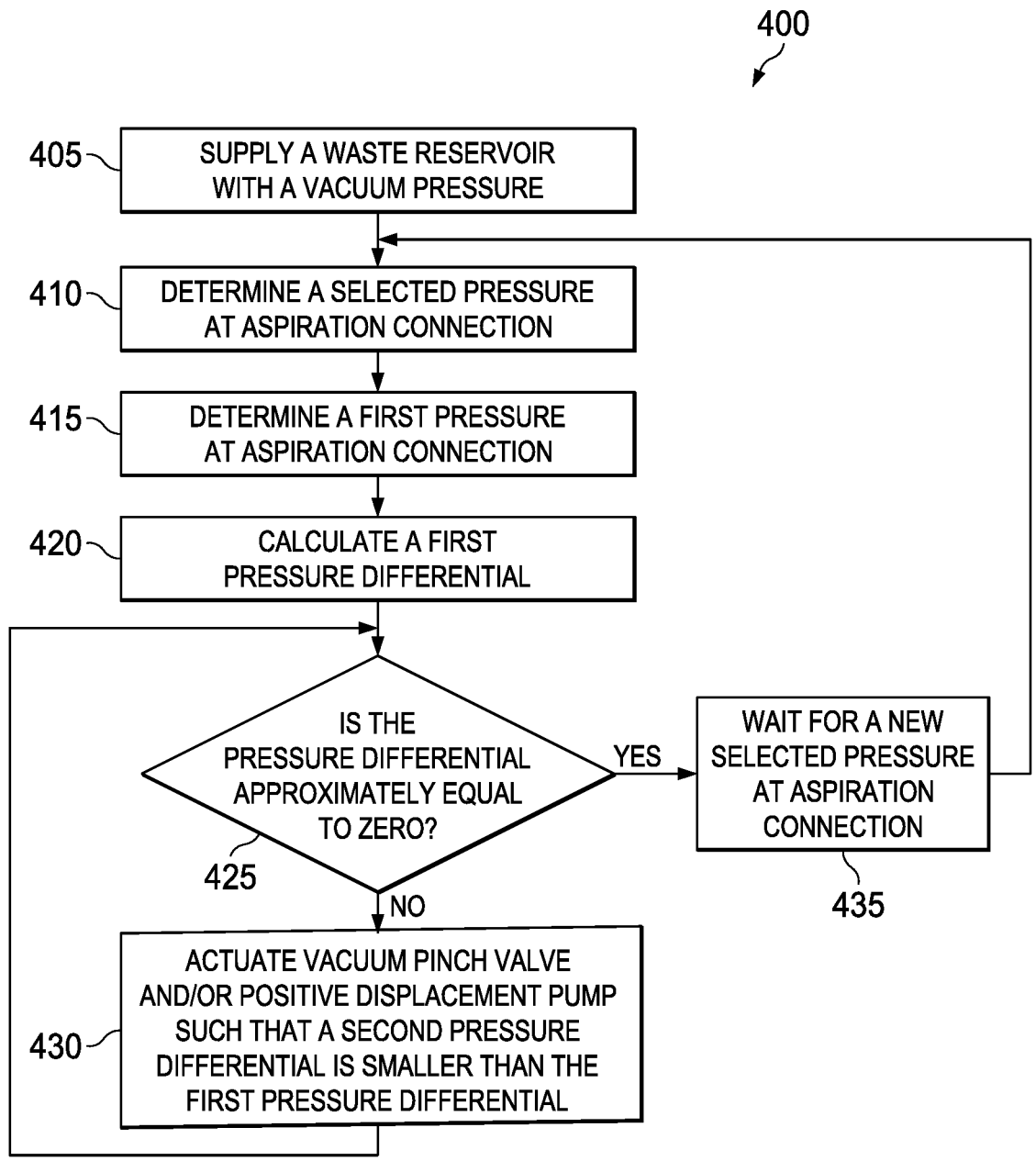
FIG. 4 is a flow chart of a method for operating the aspiration system shown in FIG. 1.

FIG. 4 is a flow chart of a method for operating an aspiration system, such as aspiration system 100 shown in FIG. 1. Method 400 may be performed by a person, various computer programs, models or any combination thereof, configured to control and analyze information from aspiration systems, apparatuses and devices. The programs and models may include instructions stored on a computer readable medium and operable to perform, when executed, one or more of the elements described below. The computer readable media may include any system, apparatus or device configured to store and retrieve programs or instructions such as a hard disk drive, a compact disc, flash memory or any other suitable device. The programs and models may be configured to direct a processor or other suitable unit to retrieve and execute the instructions from the computer readable media. For example, the programs and models may be one of the applications in applications 345 shown in FIG. 3. For illustrative purposes, method 400 is described with respect to an aspiration system similar to aspiration system 100 illustrated in FIG. 1; however, method 400 may be used to operate other aspiration systems as well.

Method 400 may begin at 405 where a vacuum pressure is supplied to a waste reservoir. The vacuum pressure that is supplied to the waste reservoir may be set at a level appropriate for the application for which the aspiration system is being used. As described above in reference to FIG. 1, the vacuum pressure that is supplied to the waste reservoir provides the vacuum capacity of the aspiration system and, thus, should be set sufficiently high to satisfy the maximum vacuum pressure that may be required in a given procedure. A user may directly set the vacuum pressure to be supplied to the waste reservoir. Alternatively, a user may set the vacuum pressure to be supplied to the waste reservoir through an automated aspiration system. The automated aspiration system then may control the vacuum pressure at the waste reservoir by communicating with a vacuum source and pressure sensors associated with the waste reservoir.

At 410, a user or an automated aspiration system may determine a selected pressure to be supplied at an aspiration connection. A user may select the pressure based on that application for which the aspiration system is being used. A user may also select various pressures throughout a procedure based on the various aspiration requirements at different stages of the procedure. A user may need to change pressure settings frequently or continuously throughout a procedure. In some instances, the selected pressure may be a vacuum pressure such that the aspiration system may be used to aspirate fluid. However, in other instances, the selected pressure may be a positive pressure such that the aspiration system may be used to reflux fluid back to the site of the procedure or to remove occlusions from the aspiration system or surgical tool. A user may directly set the selected pressure for the aspiration system. Alternatively, a user may set the selected pressure through an automated aspiration system. The automated aspiration system then may store the selected pressure in a memory, such as memory 330 shown in FIG. 3.

At 415, a user or an automated aspiration system may determine a first pressure at the aspiration connection. A vacuum pressure sensor may measure a first pressure at the aspiration connection. A user may determine the first pressure at the aspiration connection by directly observing the output of a vacuum sensor associated with the aspiration connection. Alternatively, an automated aspiration system may determine the first pressure at the aspiration connection. The automated aspiration system may make this determination by processing sensor information received from one or more pressure sensors that are associated with the aspiration connection. The first pressure at the aspiration connection may be based on the vacuum pressure that is supplied to the waste reservoir and the configuration of a vacuum pinch valve at the time that the first pressure is determined.

At 420, a user or an automated aspiration system may calculate a first pressure differential. The first pressure differential may be based on the difference between the selected pressure determined at 410 and the first pressure at the aspiration connection determined at 415. The first pressure differential may be either a positive or negative number depending on whether the first pressure is higher or lower than the selected pressure. A user may calculate the first pressure differential. Alternatively, an automated aspiration system may calculate the first pressure differential. The automated aspiration system may calculate the differential by processing the selected pressure and the first pressure according to instructions stored in a memory, and also store the differential in a memory, such as memory 330 shown in FIG. 3.

At 425, a user or an automated aspiration system may evaluate the first pressure differential calculated in 420 in order to determine whether the differential is small enough such that the first pressure is approximating the selected pressure. Thus, the differential may be described as the error between the current pressure (i.e. the first pressure) and the target pressure (i.e. the selected pressure). Depending on the application for which the aspiration system is being used, a user or an automated aspiration system may require that this error be smaller or larger. For example, the pressure may need to be controlled such that the first pressure approximates the selected pressure to within 1, 0.5, 0.1, or 0.05 pounds-per-square-inch (PSI) or other equivalent unit of pressure. A user may evaluate whether the error is acceptable by directly observing the pressure differential and comparing this to an error limit as described above. Alternatively, an automated aspiration system may make this evaluation by processing the first pressure differential and a stored error limit according to instructions stored in a memory, such as memory 330 shown in FIG. 3. If the first pressure differential is acceptable as described above, a user or an automated aspiration system may proceed to 435. However, if the first pressure differential is not acceptable, a user or an automated aspiration system may proceed to 430.

At 430, a user or an automated aspiration system may actuate the vacuum pinch valve of the aspiration system to create a second pressure at the aspiration connection. A user or an automated aspiration system may also actuate a positive displacement pump of the aspiration system. As described above in reference to FIG. 1 and FIG. 2, the vacuum pinch valve may be actuated such that an actuator increases or decreases the cross-sectional area of a fluid channel within the vacuum pinch valve. A user or an automated aspiration system may determine whether to actuate the vacuum pinch valve to increase or decrease the cross-sectional area of the fluid channel based on the selected pressure determined in 410, the first pressure determined in 415, and the first pressure differential calculated in 420. If the first pressure is greater than the selected pressure, such that the first pressure differential is a negative number, a user or an automated aspiration system may require that the second pressure be smaller in magnitude than the first pressure. In this case, the vacuum pinch valve may be actuated such that the actuator decreases the cross-sectional area of the fluid channel. If the first pressure is smaller than the selected pressure, such that the first pressure differential is a positive number, a user or an automated aspiration system may require that the second pressure be greater in magnitude than the first pressure. In this case, the vacuum pinch valve may be actuated such that the actuator increases the cross-sectional area of the fluid channel.

In either case, the second pressure should be chosen such that a second pressure differential is smaller in magnitude than the first pressure differential. The second pressure differential may be based on the difference between the selected pressure and the second pressure at the aspiration connection. The second pressure differential may be either a positive or negative number depending on whether the second pressure is higher or lower than the selected pressure. A user may calculate the second pressure differential. Alternatively, an automated aspiration system may calculate the second pressure differential. The automated aspiration system may calculate the differential by processing the selected pressure and the second pressure according to instructions stored in a memory, and also store the differential in a memory, such as memory 330 shown in FIG. 3. The second pressure differential should be smaller in magnitude than the first pressure differential, such that the second pressure at the aspiration connection more closely approximates the selected pressure than did the first pressure.

A user or an automated aspiration system may actuate the positive displacement concurrently with the vacuum pinch valve to efficiently control the pressure at the aspiration connection. As described above in reference to FIG. 1, the positive displacement pump may be actuated to provide a positive flow to the aspiration system. By providing this positive flow, the pressure at aspiration connection can be reduced in a shorter time than may be possible using only the vacuum pinch valve. The positive displacement pump may also be actuated if waste becomes lodged in the aspiration system. The positive displacement pump can be actuated to provide sufficient pressure to dislodge the waste from the aspiration system. In order to coordinate the concurrent actuation of the positive displacement pump and the vacuum pinch valve, the cut-off valve may be actuated as well. In this way, positive flow provided by the positive displacement pump and vacuum pressure provided by the vacuum pinch valve be used efficiently to achieve the desired pressure at the aspiration connection.

A user may actuate the vacuum pinch valve, the positive displacement pump and/or the cut-off valve by directly initiating actuation of the components (e.g., turning the components on/off). A user may determine when to begin and end actuation by observing the output of a vacuum sensor associated with the aspiration connection. Alternatively, an automated aspiration system may actuate the vacuum pinch valve, the positive displacement pump and/or the cut-off valve by processing the selected pressure, the first pressure, the second pressure, the first pressure differential, and the second pressure differential according to instructions stored in a memory, such as memory 330 shown in FIG. 3.

Once the vacuum pinch valve and/or the positive displacement pump have been actuated, a user or an automated aspiration system may then repeat 425. If the second pressure differential is acceptable as described above with reference to 425, a user or an automated aspiration system may proceed to 435. However, if the second pressure differential is not acceptable, a user or an automated aspiration system may proceed to step 430. If step 430 is repeated, a user or an automated aspiration system may actuate the vacuum pinch valve of the aspiration system to create a third, fourth, fifth, etc. pressure at the aspiration connection. In each case, each successive pressure should be chosen such that a successive pressure differential is smaller in magnitude than the proceeding pressure differential. Thus, 425 and 430 may need to be repeated as many times as necessary to achieve a pressure differential that is acceptable, such that a user or an automated aspiration system may proceed to 435.

At 435, a user or an automated aspiration system may wait for a change in the selected pressure. As described above in reference to 410, a user may require various pressures based on application and the stage of a procedure. In the event that the selected pressure is changed, a user or an automated aspiration system may return to 410 and repeat 410 through 435 as necessary.

Modifications, additions, or omissions may be made to method 400 without departing from the scope of the present disclosure. For example, the order of the elements may be performed in a different manner than that described and some elements may be performed at the same time. Additionally, each individual element may include additional elements without departing from the scope of the present disclosure.

Embodiments disclosed herein include:

A. An aspiration system including a waste reservoir configured to hold a vacuum pressure; an aspiration connection; and a vacuum pinch valve, including a first outlet fluidically coupled to the waste reservoir; a second outlet fluidically coupled to the aspiration connection; a fluid channel; and an actuator configured to alter a cross-sectional area of the fluid channel.

B. An automated aspiration system including a processor; a vacuum sensor coupled to the processor; an aspiration system coupled to the vacuum sensor; the aspiration system including a waste reservoir configured to hold a vacuum pressure; an aspiration connection; a vacuum pinch valve including a first outlet fluidically coupled to the waste reservoir; a second outlet fluidically coupled to the aspiration connection; a fluid channel; and an actuator coupled to the processor and configured to alter a cross-sectional area of the fluid channel; and a positive displacement pump fluidically coupled to the second outlet and the aspiration connection; and a memory communicatively coupled to the processor with computer program instructions stored therein, the instructions configured to, when executed by the processor, cause the processor to actuate the vacuum pinch valve such that a pressure at the aspiration connection is controlled.

C. A method for operating an aspiration system including supplying a waste reservoir of an aspiration system with a vacuum pressure; determining a selected pressure at an aspiration connection of the aspiration system; determining a first pressure at the aspiration connection; calculating a first pressure differential based on the selected pressure and the first pressure; and actuating a vacuum pinch valve of the aspiration system, fluidically coupled between the waste reservoir and the aspiration connection, resulting in a second pressure at the aspiration connection such that a second pressure differential based on the selected pressure and the second pressure is smaller in magnitude than the first pressure differential.

Each of embodiments A, B, and C may have one or more of the following additional elements in any combination: Element 1: a vacuum sensor fluidically coupled to the second outlet and the aspiration connection. Element 2: a positive displacement pump fluidically coupled to the second outlet and the aspiration connection. Element 3: wherein the waste reservoir is designed for a single use. Element 4: wherein the actuator comprises a solenoid. Element 5: a cut-off valve fluidically coupled between the vacuum pinch valve and the aspiration connection. Element 6: wherein the fluid channel comprises a silicone tube. Element 7: a surgical tool fluidically coupled to the aspiration connection. Element 8: wherein the waste reservoir is configured to hold a maximum vacuum pressure and the selected pressure, the first pressure, and the second pressure are each less than or equal to the maximum vacuum pressure. Element 9: wherein the instructions are further configured to cause the processor to determine a selected pressure at the aspiration connection; determine a first pressure at the aspiration connection; calculate a first pressure differential based on the selected pressure and the first pressure; and actuate the vacuum pinch valve resulting in a second pressure at the aspiration connection such that a second pressure differential based on the selected pressure and the second pressure is smaller in magnitude than the first pressure differential. Element 10: wherein actuating the vacuum pinch valve includes actuating the actuator; and altering the cross-sectional area of the fluid channel. Element 11: wherein the instructions are further configured to cause the processor to actuate the positive displacement pump resulting in a second pressure at the aspiration connection such that a second pressure differential based on the selected pressure and the second pressure is smaller in magnitude than the first pressure differential. Element 12: wherein the instructions are further configured to cause the processor to actuate the vacuum pinch valve resulting in a third pressure at the aspiration connection such that a third pressure differential based on the selected pressure and the third pressure is smaller in magnitude than the second pressure differential. Element 13: wherein altering the cross-sectional area such that the cross-sectional area increases results in the second pressure being greater than the first pressure and altering the cross-sectional area such that the cross-sectional area decreases results in the second pressure being less than the first pressure. Element 14: actuating a positive displacement pump of the aspiration system, fluidically coupled between the vacuum pinch valve and the aspiration connection, resulting in a second pressure at the aspiration connection such that a second pressure differential based on the selected pressure and the second pressure is smaller in magnitude than the first pressure differential. Element 15: actuating the vacuum pinch valve resulting in a third pressure at the aspiration connection such that a third pressure differential based on the selected pressure and the third pressure is smaller in magnitude than the second pressure differential.

The invention claimed is:

1. An aspiration system, comprising:
   a waste reservoir configured to hold a vacuum pressure;
   an aspiration connection configured to fluidically connect a surgical tool to the aspiration system;
   a vacuum pinch valve comprising:
      a first outlet fluidically coupled to the waste reservoir;
      a second outlet;
      a fluid channel connecting the first outlet and the second outlet; and
      an actuator configured to alter a cross-sectional area of the fluid channel;
   a vacuum sensor fluidically coupled to the second outlet and the aspiration connection;
   a positive displacement pump configured to generate a positive pressure at an outlet of the positive displacement pump; and
   a cut-off valve connecting the outlet of the positive displacement pump and the second outlet of the vacuum pinch valve to the aspiration connection.

2. The aspiration system of claim 1, wherein the waste reservoir is configured to hold a maximum vacuum pressure.

3. The aspiration system of claim 1, wherein the cut-off valve is a three way valve that selectively fluidically couples the outlet of the positive displacement pump or the second outlet of the vacuum pinch valve to the aspiration connection.

4. The aspiration system of claim 1, wherein the cut-off valve is a three way valve configured to at least partially fluidically couple the outlet of the positive displacement pump and at least partially fluidically couple the second outlet of the vacuum pinch valve to the aspiration connection.

5. An automated aspiration system, comprising:
a processor;
a vacuum sensor coupled to the processor;
an aspiration system coupled to the vacuum sensor, the aspiration system comprising:
a waste reservoir configured to hold a vacuum pressure;
an aspiration connection configured to fluidically connect a surgical tool to the aspiration system;
a vacuum pinch valve comprising:
  a first outlet fluidically coupled to the waste reservoir;
  a second outlet;
  a fluid channel connecting the first outlet and the second outlet; and
  an actuator coupled to the processor and configured to alter a cross-sectional area of the fluid channel; and
a positive displacement pump configured to generate a positive pressure at an outlet of the positive displacement pump;
a memory communicatively coupled to the processor with computer program instructions stored therein, the instructions configured to, when executed by the processor, cause the processor to actuate the vacuum pinch valve such that a pressure at the aspiration connection is controlled; and
a cut-off valve connecting the outlet of the positive displacement pump and the second outlet of the vacuum pinch valve to the aspiration connection.

6. The automated aspiration system of claim 5, wherein the instructions are further configured to cause the processor to:
determine a selected pressure at the aspiration connection;
determine a first pressure at the aspiration connection;
calculate a first pressure differential based on the selected pressure and the first pressure; and
actuate the vacuum pinch valve resulting in a second pressure at the aspiration connection such that a second pressure differential based on the selected pressure and the second pressure is smaller in magnitude than the first pressure differential.

7. The automated aspiration system of claim 5, wherein the instructions are further configured to cause the processor to actuate the vacuum pinch valve resulting in a third pressure at the aspiration connection such that a third pressure differential based on the selected pressure and the third pressure is smaller in magnitude than the second pressure differential.

8. The automated aspiration system of claim 5, wherein actuating the vacuum pinch valve comprises:
actuating the actuator; and
altering the cross-sectional area of the fluid channel.

9. The automated aspiration system of claim 5, wherein the instructions are further configured to cause the processor to:
determine a selected pressure at the aspiration connection;
determine a first pressure at the aspiration connection;
calculate a first pressure differential based on the selected pressure and the first pressure; and actuate the positive displacement pump resulting in a second pressure at the aspiration connection such that a second pressure differential based on the selected pressure and the second pressure is smaller in magnitude than the first pressure differential.

10. The automated aspiration system of claim 5, wherein the waste reservoir is configured to hold a maximum vacuum pressure and the pressure at the aspiration connection is less than or equal to the maximum vacuum pressure.

11. The aspiration system of claim 5, wherein the cut-off valve is a three way valve that selectively fluidically couples the outlet of the positive displacement pump or the second outlet of the vacuum pinch valve to the aspiration connection.

12. The aspiration system of claim 5, wherein the cut-off valve is a three way valve configured to at least partially fluidically couple the outlet of the positive displacement pump and at least partially fluidically couple the second outlet of the vacuum pinch valve to the aspiration connection.

13. A method for operating an aspiration system, comprising:
supplying a waste reservoir of the aspiration system with a vacuum pressure;
determining a selected pressure at an aspiration connection of the aspiration system;
determining a first pressure at the aspiration connection;
calculating a first pressure differential based on the selected pressure and the first pressure; and
actuating a vacuum pinch valve of the aspiration system, fluidically coupled between the waste reservoir and the aspiration connection, resulting in a second pressure at the aspiration connection such that a second pressure differential based on the selected pressure and the second pressure is smaller in magnitude than the first pressure differential;
actuating a positive displacement pump of the aspiration system, to generate a positive pressure at an outlet of the positive displacement pump, and
controlling a cut-off valve that fluidically couples the outlet of the positive displacement pump and the vacuum pinch valve to the aspiration connection to result in a third pressure at the aspiration connection such that a third pressure differential based on the selected pressure and the third pressure is smaller in magnitude than the first pressure differential.

14. The method for operating an aspiration system of claim 13, wherein actuating the vacuum pinch valve comprises:
actuating an actuator of the vacuum pinch valve; and
altering a cross-sectional area of a fluid channel of the vacuum pinch valve.

15. The method of operating an aspiration system of claim 14, wherein altering the cross-sectional area such that the cross-sectional area increases results in the second pressure being greater than the first pressure and altering the cross-sectional area such that the cross-sectional area decreases results in the second pressure being less than the first pressure.

16. The method for operating an aspiration system of claim 13, further comprising actuating the vacuum pinch valve resulting in a fourth pressure at the aspiration connection such that a fourth pressure differential based on the selected pressure and the fourth pressure is smaller in magnitude than the second pressure differential.

17. The method for operating an aspiration system of claim 13, wherein the waste reservoir is supplied with a maximum vacuum pressure and the selected pressure, the first pressure, and the second pressure are each less than or equal to the maximum vacuum pressure.

18. The method of claim 13, wherein the cut-off valve is a three way valve, and wherein controlling the cut-off valve comprises selectively fluidically coupling the outlet of the positive displacement pump or an outlet of the vacuum pinch valve to the aspiration connection.

19. The method of claim 13, wherein the cut-off valve is a three way valve, and wherein controlling the cut-off valve comprises at least partially fluidically coupling the outlet of the positive displacement pump and at least partially fluidically coupling an outlet of the vacuum pinch valve to the aspiration connection.

* * * * *